(12) United States Patent
Georgeff

(10) Patent No.: US 10,121,558 B2
(45) Date of Patent: Nov. 6, 2018

(54) PROCESS FOR FACILITATING THE MANAGEMENT OF CARE

(75) Inventor: Michael Peter Georgeff, Toorak (AU)

(73) Assignee: Precedence Health Care, Melbourne, Victoria (AU)

( * ) Notice: Subject to any disclaimer, the term of this patent is extended or adjusted under 35 U.S.C. 154(b) by 438 days.

(21) Appl. No.: 12/515,256

(22) PCT Filed: Nov. 23, 2007

(86) PCT No.: PCT/AU2007/001806
§ 371 (c)(1),
(2), (4) Date: May 15, 2009

(87) PCT Pub. No.: WO2008/061318
PCT Pub. Date: May 29, 2008

(65) Prior Publication Data
US 2009/0313040 A1    Dec. 17, 2009

(30) Foreign Application Priority Data
Nov. 23, 2006    (AU) ................................ 2006906527

(51) Int. Cl.
*G06Q 50/00* (2006.01)
*G16H 40/63* (2018.01)

(52) U.S. Cl.
CPC .................................. *G16H 40/63* (2018.01)

(58) Field of Classification Search
USPC ........................................ 705/2, 3; 600/300
See application file for complete search history.

(56) References Cited

U.S. PATENT DOCUMENTS

| | | | |
|---|---|---|---|
| 6,802,810 B2 * | 10/2004 | Ciarniello et al. | 600/300 |
| 7,260,480 B1 * | 8/2007 | Brown et al. | 702/19 |
| 7,957,983 B2 * | 6/2011 | Hoffman et al. | 705/2 |
| 2007/0276197 A1 * | 11/2007 | Harmon | 600/300 |
| 2008/0300917 A1 * | 12/2008 | Ryan et al. | 705/2 |
| 2009/0119337 A1 * | 5/2009 | Biedermann | 707/104.1 |

* cited by examiner

*Primary Examiner* — Luke Gilligan
(74) *Attorney, Agent, or Firm* — Jones Day

(57) ABSTRACT

In a patient care process a human patient 2 is registered with a computer system 1. The system 1 records identity details for the patient 2 against a unique identifier. The system 1 receives information indicative of the health or other condition of the patient 2 and records such information against the patient's unique identifier. A health care plan 5 is also generated and/or recorded in or by the system 1 for the patient 2 against the unique identifier. The system 1 may receive and processes electronic data 6, 7, to determine whether the patient is substantially compliant or responding adequately to the care plan 5. The system 1 then generates and at least initiates a notification 8 to the patient 2 and/or at least one suitably authorized health care provider 3.

15 Claims, 2 Drawing Sheets

PROCESS FOR FACILITATING THE MANAGEMENT OF CARE

FIELD OF INVENTION

A preferred form of this invention relates to a process for facilitating the management of care in the context of heath. Those skilled in, the art will appreciate that the invention also has other applications.

BACKGROUND

Many people suffer from medical conditions which have an adverse effect on them in terms of their quality of life and the costs involved in obtaining treatment. Some medical conditions are such that they are best treated by placing a patient on a care plan with constant monitoring and feedback. It is an object of a preferred form of the present invention to go at least some way towards facilitating this.

The term "comprising" or derivatives thereof, if and when used in this document, should be interpreted non-exclusively, eg to mean "consisting of or including".

SUMMARY OF THE INVENTION

According to one aspect of the invention there is provided a care process involving the steps of:
a) registering a plurality of healthcare providers in a computer system;
b) registering a human subject in the computer system, the system recording for that subject information as to at least:
   i. the identity of the subject; and
   ii. the subject's current physical condition;
c) the computer system allocating a unique identifier to the human subject and associating such identifier against at least some of the healthcare providers relevant to the human subject;
d) the computer system generating a personalised healthcare plan for the subject based on at least the information i and ii, and recording the healthcare plan against the unique identifier for the subject, the healthcare plan comprising computer recorded data indicating steps that need to be taken by the subject and by at least one of the healthcare providers in order to achieve compliance with the care plant
e) the computer system automatically distributing the healthcare plan to at least one of the healthcare providers for input into the healthcare plan and approval of the healthcare plan and making the healthcare plan, when approved, viewable by at least one of the healthcare providers;
f) the system receiving electronic data at least some of which has been transmitted from a remote system or a remote device associated with at least one of the healthcare providers and/or the human subject, and processing the data, such processing sufficient to indicate—
   i) whether the human subject is compliant with the healthcare plan; and/or
   ii) whether at least one physical condition of the human subject complies with one or more recorded rule(s) of the computer system;
g) the system generating and at least initiating a message which is transmitted to the subject and/or at least one of the healthcare providers, in at least one case to a remote system or to a remote device, such message comprising:
   i) a reminder as to an upcoming or missed action necessary for compliance with the subject's care plan; and/or
   ii) a report indicative of whether at least one physical condition of the subject complies with a recorded rule of the computer system; and/or
   iii) whether a specified action is advisable for the benefit of the subject.

Preferably the healthcare plan comprises information defining goals, actions and/or events deemed appropriate for the benefit of the subject Preferably step d) incorporates or is preceded by receiving base information in the computer system wherein such base information is indicative of a need or a goal of the subject.

Preferably the base information is received by the computer system electronically.

Preferably the healthcare plan is electronically generated by the computer system based on a set of rules recorded in the system, and if applicable utilising the base information.

Preferably the computer system has a facility for allowing manual or automatic modification of the healthcare plan by the subject and/or by at least one authorised party.

Preferably the at least one authorised party is one of the healthcare providers which is authorised by the computer system to participate in the healthcare plan for the benefit of the subject.

Preferably there are numerous of the healthcare providers authorised by the system to participate in the care plan for the benefit of the subject.

Preferably the computer system enables the subject and/or at least one of the healthcare providers to access, via the internet, virtual private network or other local area network, a profile which has been generated and recorded by the computer system for the subject, such profile providing information as to progress and/or history and/or current condition of the subject in relation to the healthcare plan.

Preferably the subject's profile is password protected.

Preferably the message referred to at step g) is delivered to the subject and/or to at least one of the healthcare providers by way of email, SMS, the internet, and or a mobile message distribution service such as GPRS, or any other suitable means.

Preferably the electronic data referred to at step f) is received from one or more affiliate computer systems remote from the computer system referred to at step a) and wherein the affiliate computer system(s) is/are associated with one or more of the healthcare providers.

Preferably information or data passed to and from the computer system referred to at step a) is transmitted via a secure connection in each case.

Preferably at step f) the computer system referred to at step a) generates and at least initiates the sending of a report providing statistical or population based information on the performance of a plurality of subjects and/or their care providers in terms of compliance with subject healthcare plans and benefits attained through those healthcare plans.

Preferably at least one of the healthcare providers comprises a physician.

DESCRIPTION OF THE DRAWINGS

Some preferred forms of the invention will now be described by way of example and with reference to the accompanying drawings, of which.

DETAILED DESCRIPTION

Registration

Figure 1:
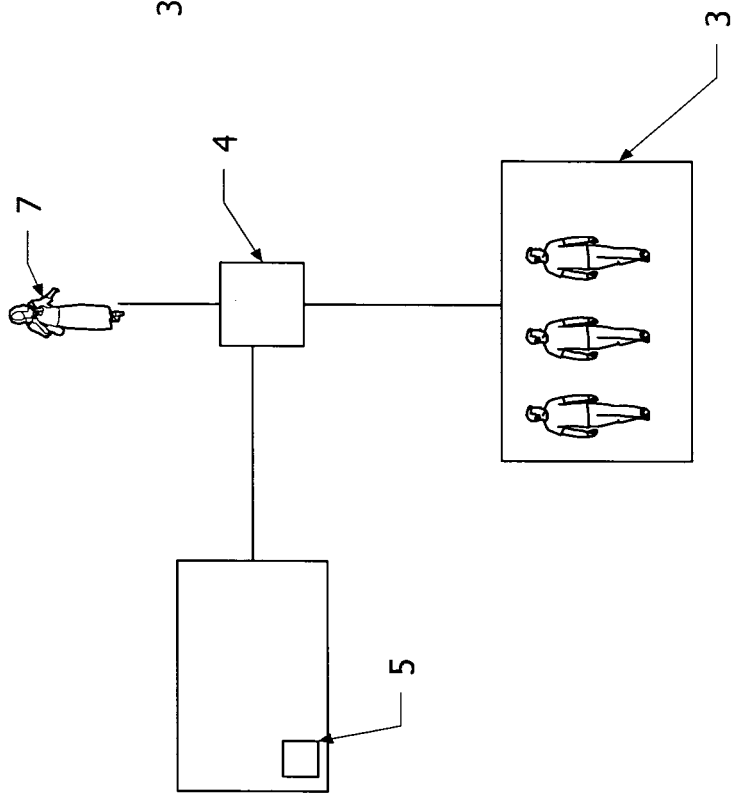
FIG. 1 schematically illustrates a patient care process.

Referring to FIG. 1, the care process comprises a main computer system 1 (eg comprising a server or servers) accessible to a patient 2 and to a plurality of authorised health care providers 3, in each case by way of the internet 4 or a suitable alternative. Patients 2 and health care providers 3 are required to register with the system 1 before they are able to participate in the patient care service provided by the system. On registration the system 1 allocates a unique identifier (eg a computer readable key) to each patient 2 and associates this with health care providers 3 relevant to that patient. The health care providers 3 may be physicians, physiotherapists, nurses, physical fitness trainers, blood lab technicians, optometrists, podiatrists, psychologists, radiologists, primary guardians, etc. Preferably the system 1 maintains or has access to a comprehensive directory or database of the health care providers 3.

Care Plan Creation

Figure 2:
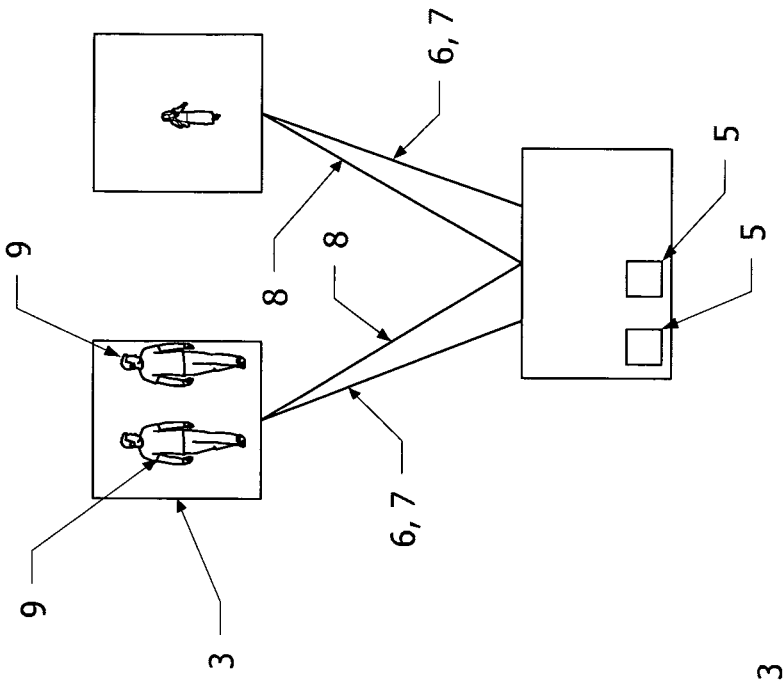
FIG. 2 schematically illustrates details of the care process.

Referring to FIG. 2, after a patient 2 is registered with the system 1, data is fed to the system sufficient to create, for that patient, a care plan 5 within the system. The data may for example include details as to the patient's current medical or other physical condition, the patient's medical history, the patient's family medical history, the patient's living or working environment, the patient's age, weight and personal habits, etc. The care plan 5 includes recorded data indicating the steps that need to be taken in order to achieve patient compliance with the care plan 5 as well as patient goals (eg a blood pressure within a specific range), etc. Such steps may include the taking of prescribed medicines at specified times, receiving medical checkups at specified times, receiving prescribed physical therapy (eg physiotherapy), submitting medical test data (eg results of blood tests), etc. The steps may include action necessary on the part of health care providers 3 rather than just the patient. In some embodiments of the invention the system 1 automatically creates a draft care plan according to processing rules based on the patient data entered into the system 1, and the plan is submitted to at least one of the health care providers for approval and/or modification before it is activated on the system. In some cases the care plan 5 may be generated to a final stage by the system 1 without the need for a health care provider to approve it. In some situations the care plan may be completely devised manually, and then details of such fed into the system.

Compliance and Wellness Data

Referring to FIG. 2, during operation of the care plan 5 the patient 2 and/or the health care providers 3 submit compliance data 6 to the system 1, preferably but not necessarily, via the internet 4. Such data 6 indicates or includes information as to steps or treatment actually taken by the patient 2 (eg medicines consumed or medical consultations attended, etc). The data 6 may also indicate or include information as to steps taken by health care providers 3. The computer system 1 processes the compliance data 6 and compares it with the patient's care plan 5 to determine whether the patient is compliant with that plan. The patient 2 and/or the health care providers 3 also submit to the system 1, preferably via the internet, wellness data 7 indicating the current physical or mental condition of the patient (for example weight, blood test results, blood pressure readings, etc). The wellness data 7 is processed by the system to determine whether the patient's medical or physical wellbeing is improving as a result of the care plan 5, for example whether it is within acceptable boundaries as specified in the care plan 5. The system 1 may also receive other information relevant to the care of the patient, for example details of new medicines or therapies, newly discovered side effects of existing medicines, etc.

Notifications

If it is determined by the system 1 that the patient 5 is non-compliant or is not responding adequately to the care plan 5, or that action by the patient or a care provider 3 is advisable, then the system sends automatic notification 8 of this to the patient 2 and/or at least one of the health care providers 3. The notification may take the form of a reminder or alert, communicated to the patient 2 and to the health care providers 3 by email, phone SMS text message or any suitable alternative means. In at least some embodiments of the invention the care plan 5 may be adjusted, automatically by the system 1 or manually, in response to a determination by the system 1 that the patient is non-compliant or has inadequate wellbeing. In some embodiments of the invention the system 1 may send patients 2 and/or health care providers 3 reminders of medicines or steps to be taken (eg appointments to attend), etc, necessary or desirable for compliance with a respective health care plan 5.

Further Features

In situations where the patient is in the care of several health care providers 3 the system 1 may provide information as to the status of a patient at any one time, avoiding complications that can arise when one health care provider is not adequately aware of the work done with the patient by other health care providers. The system 1 maintains a computerised profile of each patient 2 registered with it, and such profile can be accessed or viewed online by suitably authorised health care providers 3 and/or the respective patient 2. Each profile may include details of the notifications 8 sent for the patient, details of how the patient is responding to the care plan, the medicines taken or consultations attended by the patient, etc, and any other details relevant to the patient.

Referring to FIG. 2, preferably the system records a health care coordinator 9 for each patient. The health care coordinators are selected from the set of health care providers 3 for each patient. Different patients may have different coordinators 9, and in each case the coordinator is charged with primary responsibility for or oversight of that patient. For some patients 2 the coordinator has authority to activate a health care plan in the system and/or modify it, in each case via a network connection.

In some embodiments of the invention the system may have rules recorded in it to determine conflicts in a proposed or actual care plan, for example the prescribing of contraindicated medicines based on existing or new information, the overuse, under use, or misuse of medicines or other therapies, etc.

In some embodiments of the invention the system 1 provides population based feedback to suitably authorised health care providers or patients, etc, on performance and outcomes relevant to care plans.

The system 1 may provide for the allocation of incentives or rewards for compliance by patient's and health care providers, or for meeting predefined targets, etc.

While the internet 4 has been specifically mentioned as a means of transmitting information to and from the system 1, other means of communication can be employed as appropriate, for example a private network, a network using a TCP/IP protocol, an intranet, a virtual private network (VPN), a medical grade network, a phone network, GPRS, a mobile network and a GSM network. There may be overlap between the above items in that, for example, a mobile network may be a subset of a phone network. Optionally data communicated to or from the main system 1 conforms to the standards ICD-10, ICD-9, SNOMED-CT, CATCH, MIMS, NDC, LOINC, MeSH, UMLS, HGNC, HL7, etc.

In some embodiments of the invention the main computer system 1 has a facility to monitor use or contributions of data by the patients 2 and/or health care providers 3, and may allocate financial charges (eg debits) or service payments (eg credits) to user accounts held in the system 1, corresponding to the amount of use or contributions such parties 2, 3 make of or to the system. The main system 1 may control or contribute to the billing of the parties 2, 3.

In some embodiments of the invention the system 1 may monitor compliance with regulatory requirements, such as may be necessary for access to certain services or medicines, or for receiving rebates from Government organisations or health care insurers, etc.

Example

Figure 3:
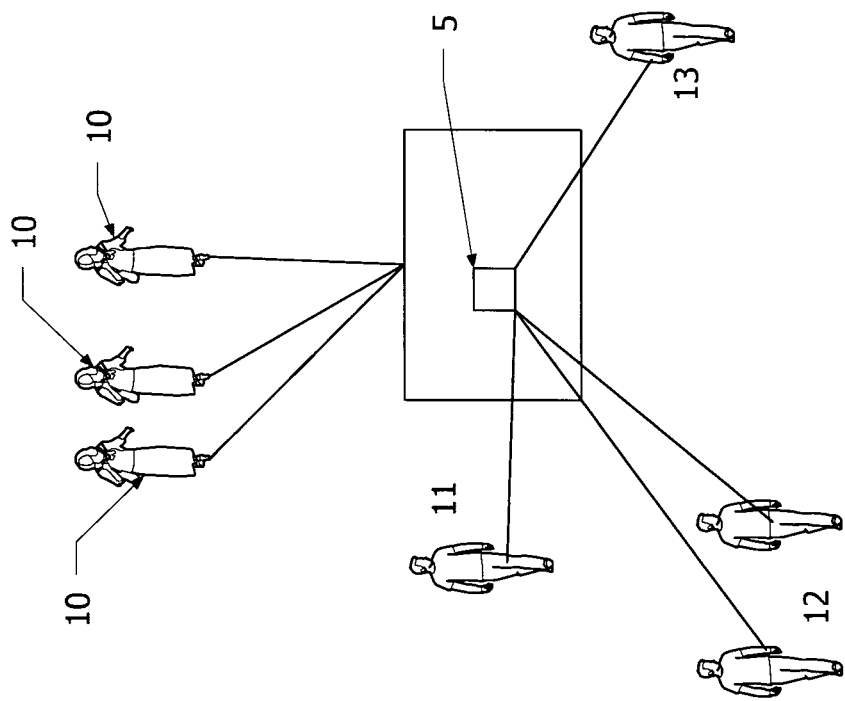
FIG. 3 schematically illustrates a particularly preferred patient care process.

Referring to FIG. 3, according to a particularly preferred embodiment of the invention there is a care process used by patients 10 with a chronic disease. A care coordinator 11 (a person) is assigned to each patient 10 and details of this are recorded in the system 1. The care coordinator 11 is a person with primary responsibility for the care of the patient under the care process and may for example be a primary care physician. He or she has responsibility for creating or modifying the patient's care plan 5.

A care team 12 made up of a group of people is assigned to each patient and details of such team and assignment are recorded in the system 1. Those that belong to the care team 12 share in responsibility for the care of a respective patient 10 in accordance with the care plan 5 corresponding to that patient. They may participate in examining the patient and may for example fill the roles of allied health worker, podiatrists, ophthalmologists, etc. In some embodiments of the invention the care team 12 may also have input into creation of the patient's care plan.

A care support team or person 13 is assigned to the patient 10 and details of this are recorded in the system 1. The care support person 13 or team may be involved in providing assistance in the creation of the care plan 5, in patient assessment, in care plan tracking, and in managing alerts and notifications.

The coordinator 11, the care team 12, and the care support person 13 may all be regarded as health care providers. Each patient may be required to give consent (eg via an internet connection) to which health care providers will be authorised to access the profile stored on the system for that patient. Authorisation of health care providers may, for example, be done through a web page where a patient is shown a list of health care providers affiliated with the system 1 and selects from these using a computer mouse or similar. The authorisation may enable some of the patient's health care providers greater access to the patient's profile than other health care providers. Alternatively, once authorised by the patient, the care coordinator 11 may select the care team 12 and the care support person 13 on behalf of the patient. The care coordinator 11 may also enter details into the system 1 to define what level of access each member of the care team 12/care support person 13 will have.

With further reference to FIG. 3, once data is fed into the system 1 for a patient 10, notification parameters (eg alerts and reminders) are recorded by the system 1. The system then sends notifications to the patient and/or at least some of the health care providers 11, 12, 13 as appropriate, in a similar way to that described previously.

In some embodiments of the invention the patient 2 may be substituted by an athlete and the care plan may comprise a training regime for that athlete. References to "health information" should thus be construed broad enough to include information as to the physical abilities or physical progress of sportspeople. In this situation the care plan can for example be a training regime and at least one care provider can be a coach or trainer.

While some preferred forms of the invention have been described by way of example it should be appreciated that modifications and improvements can occur without departing from the scope of the following claims.

The invention claimed is:

1. A care process involving the steps of:
 a) registering a plurality of healthcare providers in a computer system;
 b) registering a human subject in the computer system, the system recording for that subject information as to at least:
  i. the identity of the subject; and
  ii. the subject's current physical condition;
 c) the computer system allocating a unique identifier to the human subject and associating such identifier against at least some of the healthcare providers where said some of the healthcare providers are deemed relevant to the human subject;
 d) the computer system generating a personalised healthcare plan for the subject based on at least the information i and ii, and recording the healthcare plan against the unique identifier for the subject, the healthcare plan comprising computer recorded data indicating steps that need to be taken by the subject and by at least one of the deemed relevant healthcare providers in order to achieve compliance with the care plan;
 e) the computer system automatically distributing the healthcare plan to at least one of the deemed relevant healthcare providers for input into the healthcare plan and approval of the healthcare plan and making the healthcare plan, when approved, viewable by at least one of the deemed relevant healthcare providers;
 f) the system receiving electronic data at least some of which has been transmitted from a remote system or a remote device associated with at least one of the deemed relevant healthcare providers and/or the human subject, and processing the data, such processing sufficient to indicate—
  i) whether the human subject is compliant with the healthcare plan; and/or
  ii) whether at least one physical condition of the human subject complies with one or more recorded rule(s) of the computer system;
 g) the system generating and at least initiating a message which is transmitted to the subject and/or at least one of the deemed relevant healthcare providers, in at least one case to a remote system or to a remote device, such message comprising:
  i) a reminder as to an upcoming or missed action necessary for compliance with the subject's care plan; and/or ii) a report indicative of whether at least one physical condition of the subject complies with a recorded rule of the computer system; and/or iii) whether a specified action is advisable for the benefit of the subject.

2. A process according to claim 1, wherein the healthcare plan comprises information defining goals, actions and/or events deemed appropriate for the benefit of the subject.

3. A process according to claim 2, wherein step d) incorporates or is preceded by receiving base information in the computer system wherein such base information is indicative of a need and/or a goal of the subject.

4. A process according to claim 3, wherein the base information is received by the computer system electronically.

5. A process according to claim 4, wherein the healthcare plan is electronically generated by the computer system based on a set of rules recorded for the system, and if applicable utilising the base information.

6. A process according to claim 5, wherein the computer system has a facility for allowing manual or automatic modification of the healthcare plan by the subject and/or by the at least one authorised party.

7. A process according to claim 6, wherein the at least one authorised party is one of the deemed relevant healthcare providers which is authorised by the computer system to participate in the healthcare plan for the benefit of the subject.

8. A process according to claim 7, wherein there are numerous of the deemed relevant healthcare providers authorised by the system to participate in the healthcare plan for the benefit of the subject.

9. A process according to claim 1, wherein the computer system enables the subject and/or at least one of the deemed relevant healthcare providers to access, via the internet, virtual private network or other local area network, a profile which has been generated and recorded by the computer system for the subject, such profile providing information as to progress and/or history and/or current condition of the subject in relation to the healthcare plan.

10. A process according to claim 9, wherein the subject's profile is password protected.

11. A process according to claim 1, wherein the message referred to at step g) is delivered to the subject and/or to the at least one of the deemed relevant healthcare providers by way of email, SMS, the internet, or a mobile message service.

12. A process according to claim 1, wherein the electronic data referred to at step f) is received from one or more affiliate computer systems remote from the computer system referred to at step a) and wherein the affiliate computer system(s) is/are associated with one or more of the deemed relevant healthcare providers.

13. A process according to claim 1, wherein information or data passed to and from the computer system referred to at step a) is transmitted via a secure connection in each case.

14. A process according to claim 1, wherein at step f) the computer system referred to at step a) generates and at least initiates the sending of a report providing statistical or population based information on the performance of a plurality of subjects and/or their care providers in terms of compliance with subject healthcare plans and benefits attained through those healthcare plans.

15. A process according to claim 1, wherein at least one of the deemed relevant healthcare providers comprises a physician.

* * * * *